(12) United States Patent
Kishida et al.

(10) Patent No.: US 7,905,598 B2
(45) Date of Patent: Mar. 15, 2011

(54) OPHTHALMOLOGIC PHOTOGRAPHING APPARATUS

(75) Inventors: Nobuyoshi Kishida, Musashino (JP); Toshiaki Okumura, Tokyo (JP); Hajime Nakajima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/768,547

(22) Filed: Apr. 27, 2010

(65) Prior Publication Data

US 2010/0277690 A1    Nov. 4, 2010

(30) Foreign Application Priority Data

Apr. 30, 2009 (JP) ................. 2009-111212

(51) Int. Cl.
*A61B 3/14* (2006.01)
*G03B 29/00* (2006.01)
(52) U.S. Cl. .............. 351/206; 351/221; 396/18
(58) Field of Classification Search .......... 351/206, 351/205, 211, 208, 209, 210, 221; 396/18
See application file for complete search history.

(56) References Cited

U.S. PATENT DOCUMENTS

| 5,594,512 A | 1/1997 | Yoneda |
| 6,546,198 B2 * | 4/2003 | Ohtsuka ............ 396/18 |
| 7,300,154 B2 * | 11/2007 | Ono ................ 351/206 |
| 7,331,673 B2 * | 2/2008 | Ono ................ 351/221 |

FOREIGN PATENT DOCUMENTS

| JP | 9-131316 A | 5/1997 |
| JP | 3386258 B2 | 3/2003 |

* cited by examiner

*Primary Examiner* — Hung X Dang
(74) *Attorney, Agent, or Firm* — Canon U.S.A., Inc., IP Division

(57) ABSTRACT

An ophthalmologic photographing apparatus includes an imaging unit configured to capture a fundus image of a subject's eye to output an image signal, a projection unit configured to intermittently project an index light flux onto the subject's eye in synchronization with the image signal from the imaging unit, and an image recording unit configured to record the image signal from the imaging unit as a moving image.

7 Claims, 5 Drawing Sheets

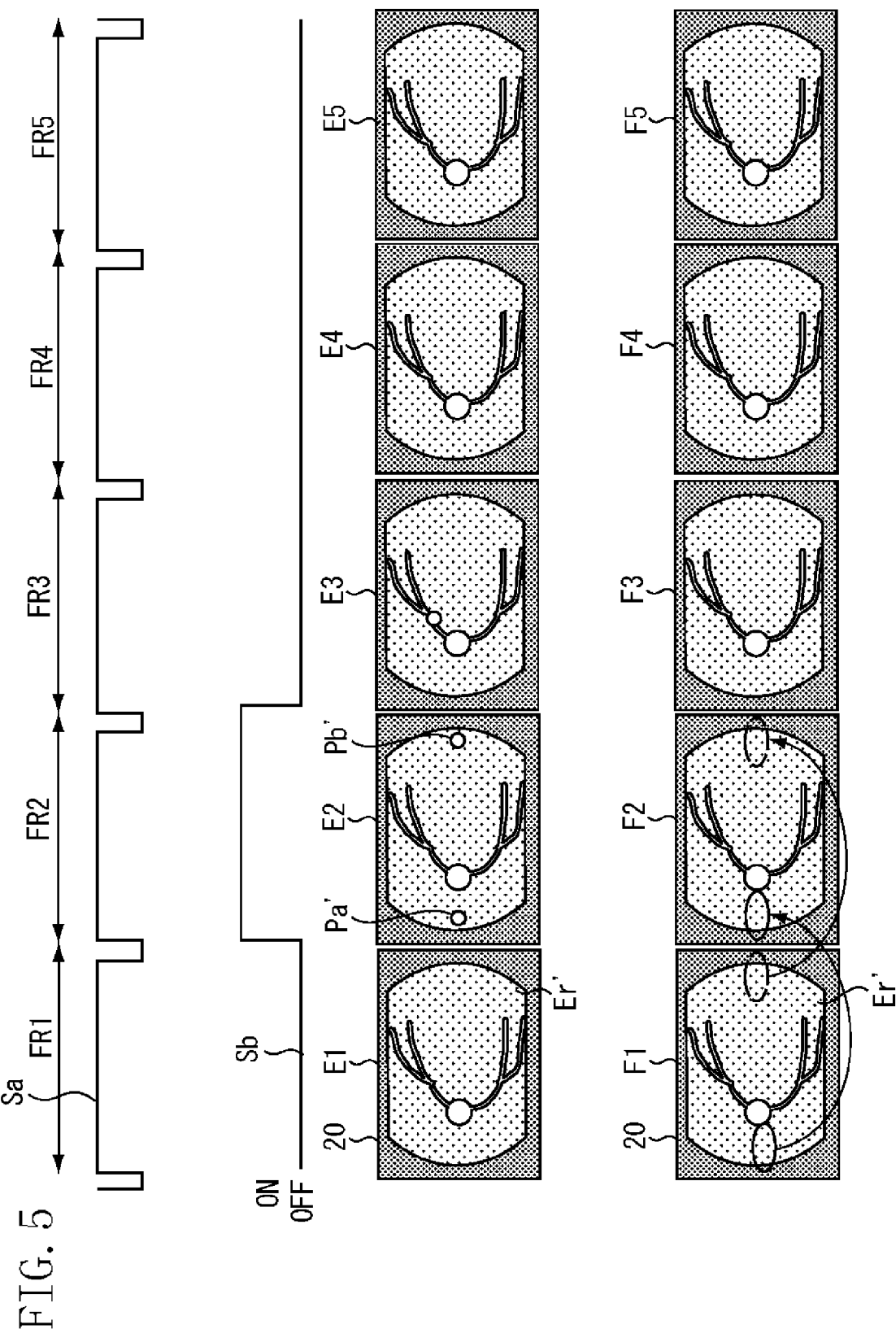

OPHTHALMOLOGIC PHOTOGRAPHING APPARATUS

BACKGROUND OF THE INVENTION

1. Field of the Invention

The present invention relates to an ophthalmologic photographing apparatus that records an image while allowing observing a subject's eye.

2. Description of the Related Art

A fundus camera that photographs the fundus of the subject's eye has widely been known as an ophthalmologic photographing apparatus. There has been known a fundus camera having a plurality of photographing modes for observing the subject's eye and making a photograph according to the purpose of an inspection, including a color photography, fluorescence angiography (FAG) (visible photofluorography), indocyanine green (ICG) (near-infrared photofluorography), etc.

In the photography by the fundus camera, the operation distance between the subject's eye and the fundus camera is to minutely be adjusted. Therefore, an alignment index is projected on the subject's eye, and the alignment adjustment is carried out with the use of the index image. Japanese Patent Application Laid-Open No. 9-131316 discusses that, to distinguish the alignment index from a flare, a plurality of alignment indexes are projected on the subject's eye, wherein each of these indexes is set to have a different brightness, or each of these indexes is flashed with a different cycle or different phase.

The photofluorography such as FAG or ICG is utilized to find a lesion region of the fundus by examining the circulating condition of blood in fundus blood vessels. In the photofluorography, the fluorescent fundus image cannot be observed until the fluorescent agent reaches the fundus blood vessels after intravenously administering the fluorescent agent, which is in several seconds to tens of seconds. Therefore, the operation distance between the subject's eye and the fundus camera is adjusted with the use of the alignment index.

In the photofluorography, a diagnosis, in which a moving image after the fluorescent agent is intravenously administered is recorded and the recorded moving image is interpreted, is an effective method. However, in the diagnosis described above, the alignment index recorded on the moving image overlaps the fundus image, with the result that the desired fundus portion cannot be confirmed.

In order to solve the above issue, Japanese Patent No. 3386258 discusses an ophthalmologic photographing apparatus in which an alignment index is projected only in a predetermined time, which is the time until the intravenously administered fluorescent agent reaches the fundus blood vessels, and the alignment index is turned off or dimmed after the lapse of the predetermined time.

However, the ophthalmologic photographing apparatus discussed in Japanese Patent No. 3386258 has a situation that the operation distance between the subject's eye and the fundus camera with the use of the alignment index cannot satisfactorily be adjusted. In the ophthalmologic photographing apparatus discussed in Japanese Patent No. 3386258, the timing at which the fluorescent fundus image can be observed is shifted from the time when the alignment index is projected. Therefore, the alignment index might be imaged when the fluorescent fundus image can be observed.

SUMMARY OF THE INVENTION

The present invention is directed to an ophthalmologic photographing apparatus that is capable of correctly adjusting the operation distance between the subject's eye and the fundus camera with the use of the alignment index when a moving image is recorded, and that is capable of allowing an operator to confirm a desired fundus portion without the hindrance by the alignment index when the moving image is interpreted.

According to an aspect of the present invention, an ophthalmologic photographing apparatus includes an imaging unit configured to capture a fundus image of a subject's eye to output an image signal, a projection unit configured to intermittently project an index light flux onto the subject's eye in synchronization with the image signal from the imaging unit, and an image recording unit configured to record the image signal from the imaging unit as a moving image.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 5 is a timing chart according to a third exemplary embodiment of the present invention.

DESCRIPTION OF THE EMBODIMENTS

Various exemplary embodiments, features, and aspects of the invention will be described in detail below with reference to the drawings.

Figure 1:
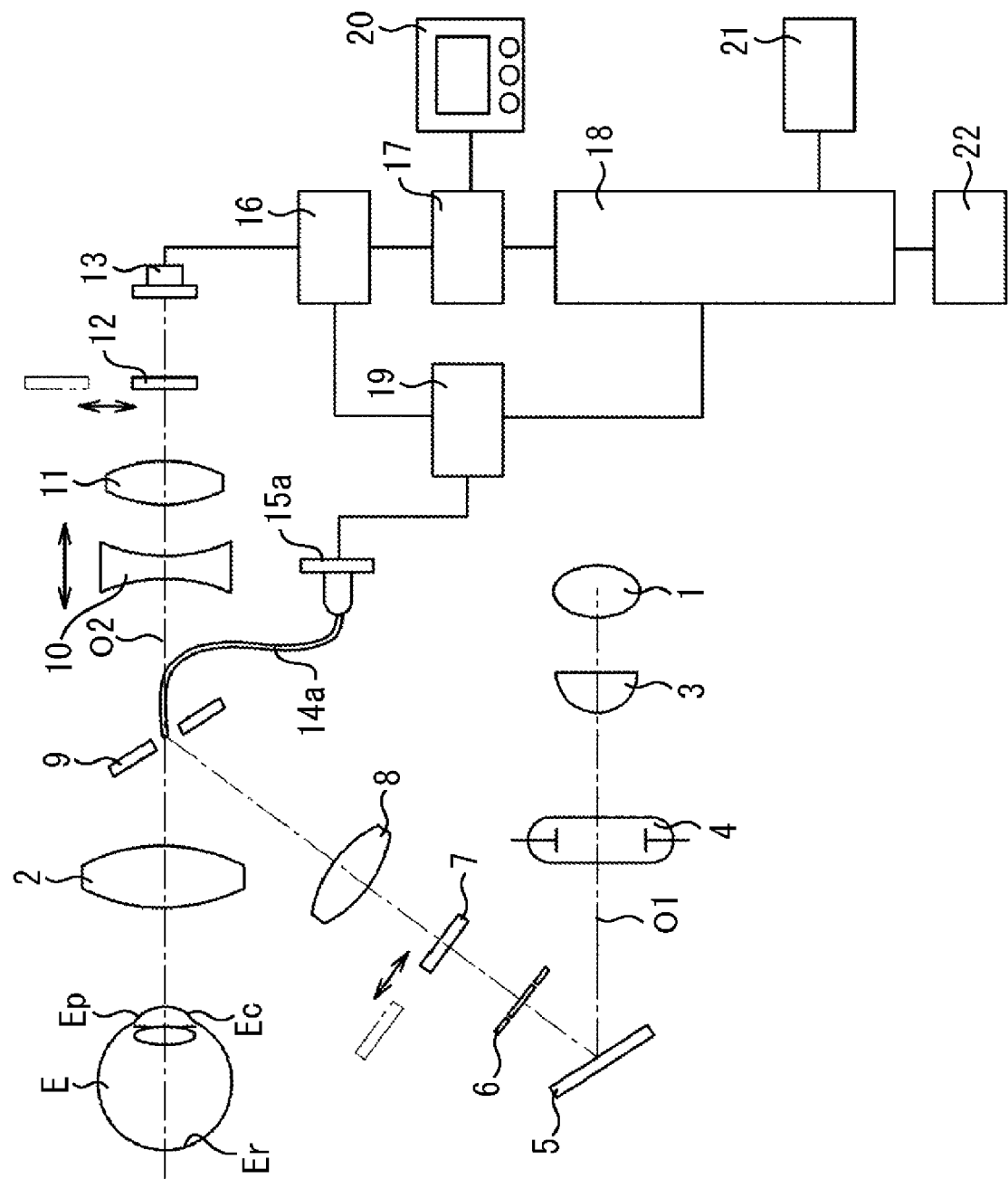
FIG. 1 is a diagram illustrating a configuration of an ophthalmologic photographing apparatus according to a first exemplary embodiment of the present invention.

FIG. 1 is a diagram illustrating a configuration of an ophthalmologic photographing apparatus according to a first exemplary embodiment of the present invention. An observation light source 1, a condenser lens 3, a photographing light source 4, and a mirror 5 are arranged on an optical path O1 from the observation light source 1 to an objective lens 2, which is located before a subject's eye E. A diaphragm 6 having an annular opening, an FAG exciter filter 7 that can be inserted to or removed from the optical path, a relay lens 8, and a perforated mirror 9 are sequentially arranged in the reflecting direction of the mirror 5. The above components 1 to 9 constitute a fundus illumination optical system.

A focusing lens 10, a photographic lens 11, an FAG barrier filter 12 that can be inserted to or removed from the optical path and that can transmit only fluorescence, and an image sensor 13 composed of a charge-coupled device (CCD) are sequentially arranged on an optical path O2 behind the perforated mirror 9. The above components 10 to 13 constitute a fundus photographing optical system.

An emission end of a light guide 14a, which guides an index light flux, is arranged at the position shifted from the optical path O2 in the vicinity of the hole of the perforated mirror 9 in the lateral direction. An LED light source 15a for lighting the alignment index is connected to the input end of the light guide 14a. An emission end of a light guide 14b (not illustrated) is arranged at the position symmetric with the emission end of the light guide 14a to the optical path O2. An LED light source 15b (not illustrated) having the same wavelength as that of the LED light source 15a is connected to the input end of the light guide 14b. The light emitted from the LED light sources 15a and 15b has the wavelength transmittable through the FAG barrier filter 12. These components constitute an alignment-index projecting optical system.

An output of the image sensor 13 is connected to a system control unit 18, which controls the entire fundus camera, via an accumulated charge reading unit 16 and an image signal processing unit 17. The accumulated charge reading unit 16 is connected to an index control unit 19, which detects the timing of accumulating the charges. A display unit 20 that displays the photographed image, an operation switch unit 21, and an image recording unit 22 that can record a moving image are connected to the image signal processing unit 17. The LED light sources 15a and 15b are connected to the system control unit 18 via the index control unit 19 to make flashing control of alignment indexes Pa and Pb.

During the observation of the fundus, the illumination light emitted from the observation light source 1 passes through the condenser lens 3 and the photographing light source 4, and is reflected on the mirror 5. The reflection light reflected on the mirror 5 passes through the diaphragm 6, the FAG exciter filter 7, and the relay lens 8, reflects on the peripheral portion of the perforated mirror 9, and then, illuminates the fundus Er of the subject's eye E through the objective lens 2. The reflection light from the fundus Er passes through the objective lens 2, the hole of the perforated mirror 9, the focusing lens 10, and the photographic lens 11, and is then focused on the imaging plane of the image sensor 13. Since the FAG barrier filter 12 is removed from the fundus photographing optical system during the observation, the reflection light from the fundus Er by the wavelength light passing through the FAG exciter filter 7 can be observed as a fundus image.

The index light flux from the LED light sources 15a and 15b emitted from the emission ends of the light guides 14a and 14b is projected on the subject's eye E through the objective lens 2 as the alignment indexes Pa and Pb. When the operation distance between the subject's eye E and the fundus camera is appropriate, the reflected image of the index light flux reflected on the cornea of the subject's eye E becomes parallel light, and forms the respective index images on the imaging plane of the image sensor 13 through the same optical path as that of the light of the illumination light flux reflected on the fundus.

The accumulated charge reading unit 16 retains the accumulated charges of the image sensor 13 after the photoelectric conversion. The accumulated charge reading unit 16 reads the signal as continuously doing the operation of reading the accumulated charges and clearing the retained charges, and outputs the resultant to the image signal processing unit 17. The image signal processing unit 17 performs an observation mode process under the control from the system control unit 18, when the mode is the observation mode. Specifically, during the observation, the image signal processing unit 17 executes the process of electrically adding an alignment mark M, which is the index for the operation distance between the subject's eye E and the fundus camera, to the fundus image that is formed by the accumulated charges of the image sensor 13. The image signal processing unit 17 then outputs the observation image to the display unit 20.

Figure 2:
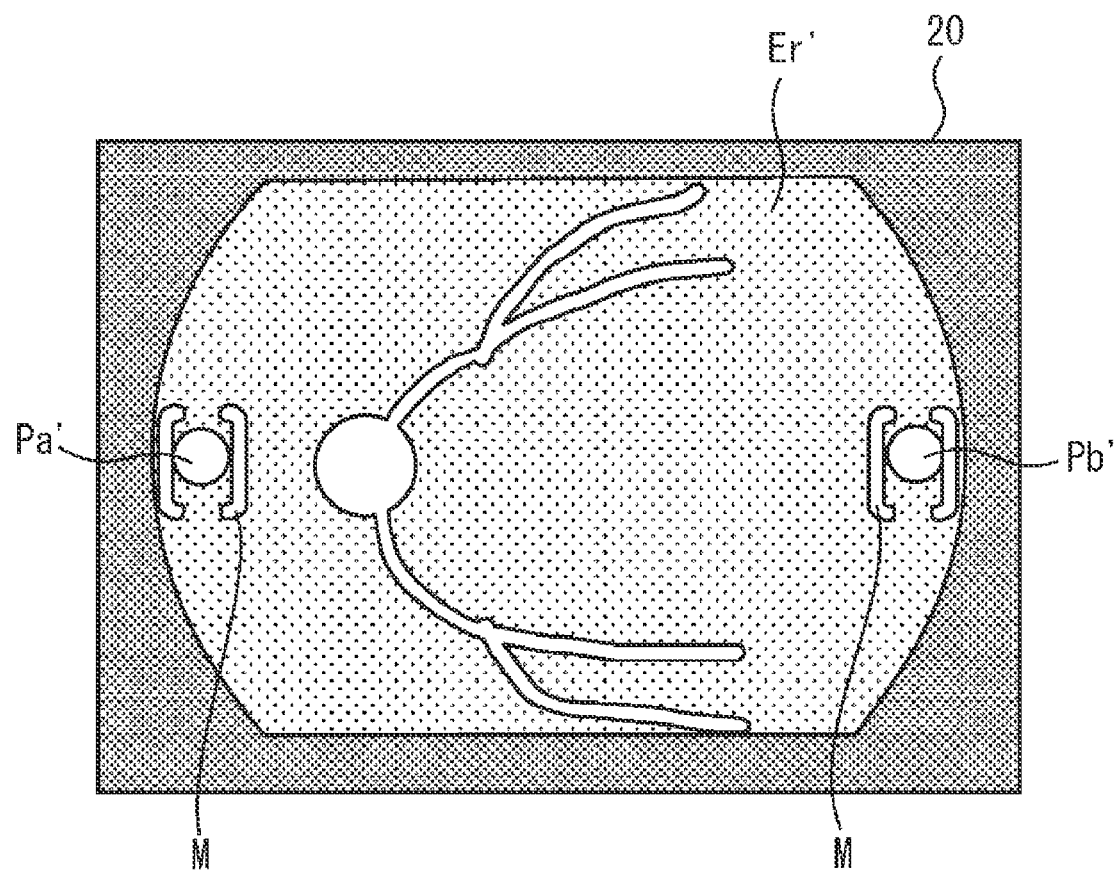
FIG. 2 is an explanatory view of an observation image.

As illustrated in FIG. 2, the fundus image Er' illuminated by the observation light source 1, the alignment mark M, and the alignment index images Pa' and Pb' by the alignment indexes Pa and Pb on the surface of the cornea are displayed on the display unit 20 when the fundus is observed. An operator operates a stage portion that can move the entire optical portion of the fundus camera illustrated in FIG. 1 to allow the index images Pa' and Pb' to agree with the alignment mark M, thereby adjusting the operation distance between the subject's eye E and the fundus camera.

In this case, the operator operates the focusing lens 10 to make a focus adjustment by using the reflection light of a focus index (not illustrated) projected on the fundus Er. The flashing control similar to that of the alignment indexes Pa and Pb can be made by connecting the focus-index light source to the index control unit 19. In the present exemplary embodiment, the focus index will not be described.

Figure 3:
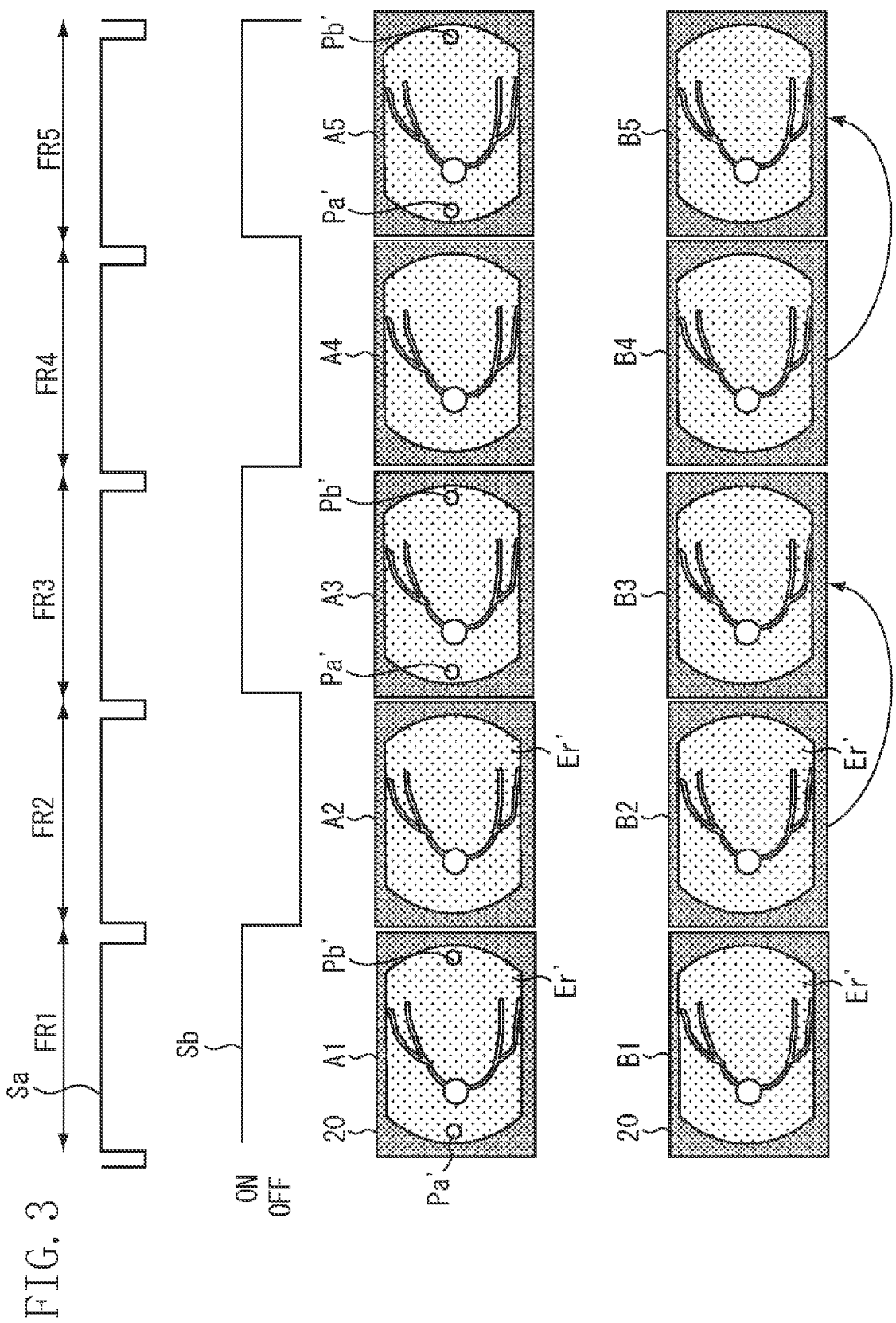
FIG. 3 is a timing chart according to the first exemplary embodiment.

FIG. 3 illustrates a timing chart of the control during the alignment according to the first exemplary embodiment. A synchronous signal Sa indicates a timing of clearing the accumulated charges on the accumulated charge reading unit 16. For example, the timing is repeated in the period of 30 Hz. As described above, the operation of reading the accumulated charges and the operation of clearing the charges are made in the accumulated charges reading unit 16. Therefore, the synchronous signal Sa is an accumulation start signal indicating the period of accumulating the charges on the image sensor 13. A flash signal Sb is generated by the index control unit 19 in synchronization with the synchronous signal Sa for making the flash control of the LED light sources 15a and 15b. When the flash signal Sb is turned on, the LED light sources 15a and 15b are lighted on, while when the flash signal Sb is turned off, the LED light sources 15a and 15b are lighted off, whereby the alignment indexes Pa and Pb are projected on the subject's eye E in an intermittent projection period.

Observation images A1 to A5 indicate observation images of frames FR1 to FR5 displayed on the display unit 20. The frames FR1 to FR5 are determined according to the period of the synchronous signal Sa. This period agrees with the period of accumulating the charges on the image sensor 13. In the frame FR1, the flash signal Sb is turned on to display the index images Pa' and Pb', while in the frame FR2, the flash signal Sb is turned off to allow the index images Pa' and Pb' not to be displayed. Similarly, the flash signal Sb is turned on in the frame FR3, turned off in the frame FR4, and turned on in the frame FR5. This operation is repeated. The system control unit 18 stores the flash period described above, which can be for the interpretation of the image as described below. The alignment mark M may be displayed on all frames FR1 to FR5, or may be displayed on only the frames FR1, FR3, and FR5 on which the index images Pa' and Pb' are displayed.

According to this control, the observation images A1, A3, and A5 on which the index images Pa' and Pb' are displayed and the observation images A2 and A4 on which the index images Pa' and Pb' are not displayed are alternately displayed on the display unit 20 during the observation. Accordingly, when the observation images A1 to A5 are continuously seen, the fundus image Er' can be observed together with the alignment mark M and the index images Pa' and Pb'. Since the synchronous signal Sa is repeated at the cycle of 30 Hz, the operator can visually confirm the index images Pa' and Pb' displayed on the display unit 20 as they are approximately continuously lighted on.

When the operation distance between the subject's eye E and the fundus camera is not appropriate, the index images Pa' and Pb' cannot be observed, or the index images Pa' and Pb' are observed at the position shifted from the alignment mark M. In this case, the operator is to adjust the operation distance between the subject's eye E and the fundus camera. Therefore, as illustrated in FIG. 2, the operation distance between the subject's eye E and the fundus camera is adjusted with the index images Pa' and Pb' agreed with the alignment mark M.

When the alignment and the focus adjustment, the description of which is not described, are completed, the operator administers the fluorescent agent to the subject, and at the same time, operates a timer switch provided in the operation switch unit 21. According to this operation, the system control unit 18 inserts the FAG barrier filter 12 into the fundus photographing optical system, and lights on the photographing light source 4, so that the photography of the fundus Er' can be carried out. The light flux emitted from the photographing light source 4 is reflected on the mirror 5, and then, made incident on the imaging plane of the image sensor 13 through the path same as the path of the observation light.

The fluorescent fundus image cannot be observed in several seconds to tens of seconds, which is the period after the FAG barrier filter 12 is inserted into the fundus photographing optical system and until the fluorescent agent reaches the fundus blood vessels after the intravenous administration of the fluorescent agent. However, in the first exemplary embodiment, the index control unit 19 continuously executes the flash control of the LED light sources 15a and 15b having the wavelength transmittable through the FAG barrier filter 12, so that the index images Pa' and Pb' and the alignment mark M can be observed. Accordingly, even during the period from when the fluorescent agent is intravenously administered to when the fluorescent agent reaches the fundus blood vessels, the operation distance between the subject's eye E and the fundus camera can be adjusted.

The fundus image Er' after the fluorescent agent reaches the fundus blood vessels after the intravenous administration of the fluorescent agent appears as an image of the fundus blood vessels that is contrast-imaged by the fluorescent agent. Therefore, the fundus image Er', the index images Pa' and Pb', and the alignment mark M can be observed as in the alignment.

On the other hand, during the observation, the observation image is recorded on the image recording unit 22 by the output from the image sensor 13 upon the photographing according to the control from the system control unit 18. The observation images including the images A1, A3, and A5 having the index images Pa' and Pb' displayed thereon are recorded in association with the projection condition of the index images Pa' and Pb'. Since the alignment mark M is not contained in the output data of the image sensor 13, it is not recorded. However, the alignment mark M may be recorded together with the index images Pa' and Pb'.

After the FAG photography is completed, the operator operates again the timer switch provided in the operation switch unit 21 to end the photography. According to this operation, the system control unit 18 removes the FAG barrier filter 12 from the fundus photographing optical system, and ends the image recording operation to the image recording unit 22. When the operator operates a moving-image reproduction switch (not illustrated) provided in the operation switch unit 21 to interpret the image after the FAG photography, the mode becomes the reproduction mode based upon the recording of the projection condition of the index images Pa' and Pb' stored in the image recording unit 22.

The image signal processing unit 17 performs a process of outputting the observation images A1, A2, . . . transmitted from the image recording unit 22 as reproduction images B1, B2, . . . . The observation images A2 and A4 on which the index images Pa' and Pb' as illustrated in FIG. 3 are not displayed are defined as reproduction images B2 and B4 of the corresponding timing. In the reproduction images B1, B3, and B5 corresponding respectively to the observation images A1, A3, and A5 having the index images Pa' and Pb' displayed thereon, the reproduction images . . . , B2, B4 in which the index images Pa' and Pb' are not displayed are used as the reproduction images. Specifically, the reproduction images B1, B3, and B5 are complemented with the use of the corresponding reproduction images immediately before the reproduction images B1, B3, and B5.

According to this control, the reproduction images on which the index images Pa' and Pb' are not displayed can be displayed on the display unit 20. Therefore, this control can prevent the situation in which the desired fundus portion cannot be confirmed because the index images Pa' and Pb' overlap the fundus image Er' when the image is to be interpreted.

When the same frame resolution as that during the observation is needed during the interpretation of the FAG image, the apparatus can be configured to include an operation switch, which cancels the process at the image signal processing unit 17 in the reproduction mode, to the operation switch unit 21. In this case, the alignment state during the photography can be confirmed through the confirmation of the index images Pa' and Pb' by displaying the alignment mark M.

The same control as the control for the alignment index can be executed for the focus index control, whose description is not described.

Figure 4:
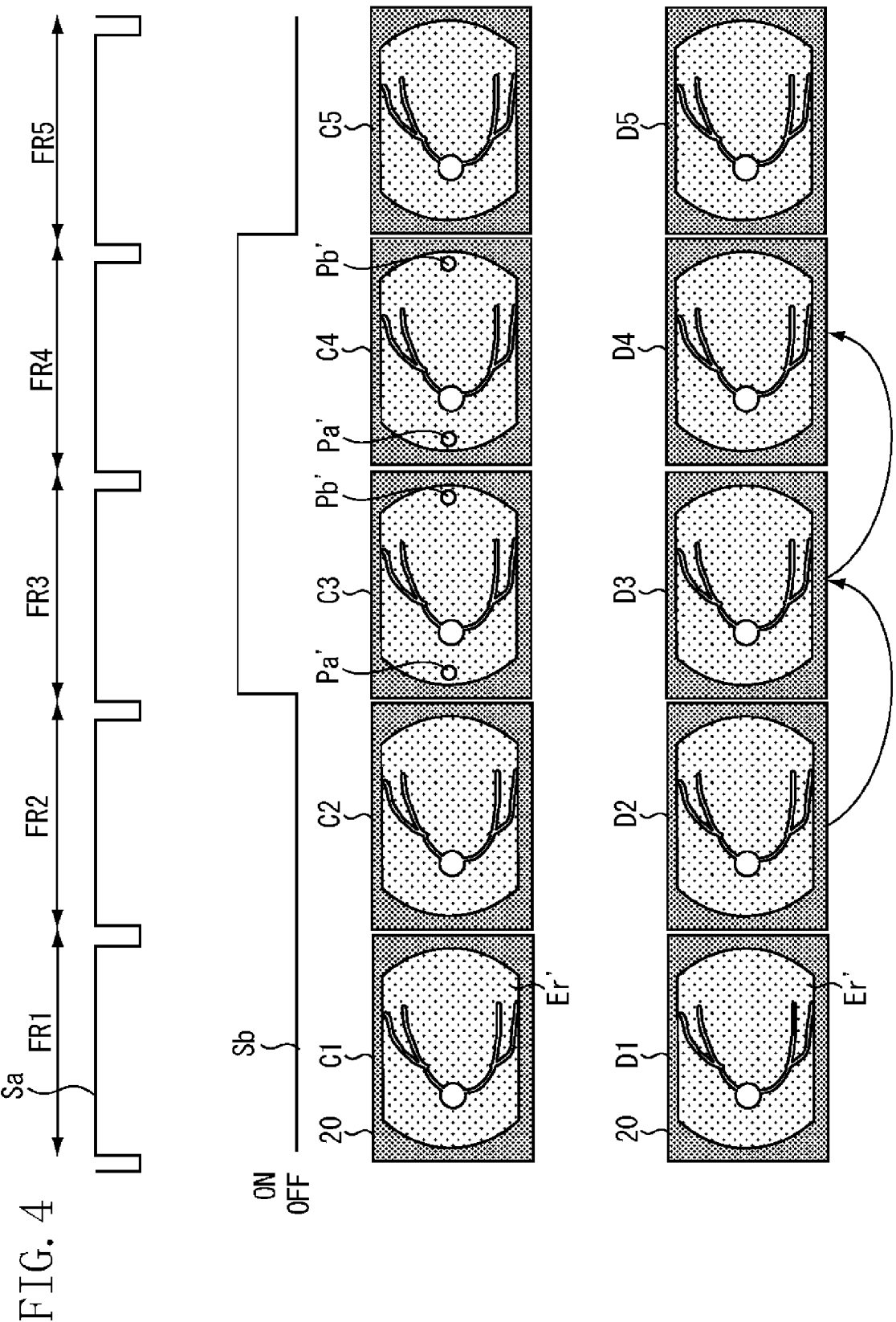
FIG. 4 is a timing chart according to a second exemplary embodiment of the present invention.

The configuration of a fundus camera according to a second exemplary embodiment is similar to that in the first exemplary embodiment. FIG. 4 illustrates a timing chart in the second exemplary embodiment. In the second exemplary embodiment, the index control unit 19 executes control with the flash signal Sb in synchronization with the synchronous signal Sa. The control is as described below. Specifically, the flash signal Sb is turned off during the period of projecting the frame FR1, and the flash signal Sb is turned off during the period of projecting the frame FR2. Similarly, the flash signal Sb is turned on during the projecting period of the frame FR3, turned on during the projecting period of the frame FR4, and turned off during the projecting period of the frame FR5.

According to the control described above, the observation image in which the frames having the index images Pa' and Pb' displayed thereon such as the observation images C3 and C4 are continuous and the observation image in which the frames not having the index images Pa' and Pb' displayed thereon such as the observation images C1 and C2 are continuous are observed. Accordingly, when the observation images C1 to C5 are continuously observed, the fundus image Er' is observed together with the flashing index images Pa' and Pb' on the display unit 20.

In the first exemplary embodiment, the operator can confirm the index images Pa' and Pb' displayed on the display unit 20 as they are approximately continuously lighted on. On the other hand, in the second exemplary embodiment, the index images Pa' and Pb' are confirmed as the flashing images, since the frames having the index images Pa' and Pb' displayed thereon and the frames not having the images Pa' and Pb' displayed thereon are continuous. The flashing period described above allows the operator to clearly distinguish the index images and the harmful rays.

In the second exemplary embodiment, when the operation distance between the subject's eye E and the fundus camera is appropriate as in the first exemplary embodiment, the flashing index images Pa' and Pb' can be observed together with the fundus image Er', so that the operator can confirm the operation distance between the subject's eye E and the fundus camera while observing the fundus image Er'. The observation of the fundus in FAG and the operation of recording the moving image are similar to as those in the first exemplary embodiment.

The system control unit 18 reproduces the observation image recorded in the image recording unit 22, and changes the image signal processing unit 17 from the observation mode to the reproduction mode. In the process at the image signal processing unit 17 in the reproduction mode, the reproduction image D2 before the frame at this timing, on which the index images Pa' and Pb' are not displayed, is used as the reproduction images D3 and D4 at this timing, instead of the observation images C3 and C4 on which the index images Pa' and Pb' are displayed.

According to the control described above, the reproduction images D1 to D5 on which the index images Pa' and Pb' are not displayed can be obtained during the observation of the fundus in FAG and during the operation of recording the moving image, instead of the observation images C1 to C5 on which the index images Pa' and Pb' are displayed as flashing. Accordingly, the control described above can prevent the situation in which the desired fundus portion cannot be confirmed since the projected portions of the index images Pa' and Pb' overlap the fundus image Er' when the image is to be interpreted.

A method can be considered in which the flashing manner of the index images Pa' and Pb' is changed by the operation of the timer switch when the fluorescent agent is intravenously administered to the subject as described in the first exemplary embodiment. For example, the apparatus may be configured to to be capable of confirming the index images Pa' and Pb' as they are approximately continuously lighted on, as in the first exemplary embodiment, before the operation of the timer switch, and to be capable of confirming the flashing index images Pa' and Pb', as in the second exemplary embodiment, after the timer switch is operated. There are various methods considered for the combination of the flashing manners of the index images Pa' and Pb' before and after the operation of the timer switch.

FIG. 5 is a timing chart according to a third exemplary embodiment of the present invention. In the timing chart illustrated in FIG. 5, the duty ratio, which is the ratio of the light-on and light-off of the index images Pa' and Pb', is set to be 1:3 from 2:2 in the second exemplary embodiment. The duty ratio can optionally be set.

The index control unit 19 executes control by the flash signal Sb in synchronization with the synchronous signal Sa. The flash signal Sb is turned off during the period of projecting the frame FR1, turned on during the period of projecting the frame FR2, and turned off during the period of projecting the frames FR3 to FR5.

According to the control described above, the observation images E1 to E5 include the observation image E2 on which the index images Pa' and Pb' are displayed, and the observation images E1 and E3 to E5 on which the index images Pa' and Pb' are not displayed. Therefore, when the observation images E1 to E5 are continuously observed, the fundus image Er' is observed together with the flashing index images Pa' and Pb' on the display unit 20, but the flashing period of the index images Pa' and Pb' is different from that in the second exemplary embodiment.

When the operation distance between the subject's eye E and the fundus camera is appropriate as in the second exemplary embodiment, the flashing index images Pa' and Pb' can be observed together with the fundus image Er', so that the operator can confirm the operation distance between the subject's eye E and the fundus camera while confirming the fundus image Er'.

In the process at the image signal processing unit 17 in the reproduction mode, the reproduction image F1, in which the index images Pa' and Pb' are not displayed and which is the image immediately before the reproduction image F1, is complemented as the reproduction image F2, instead of the observation image F2 on which the index images Pa' and Pb' are displayed.

According to the control described above, the index images Pa' and Pb', which are displayed as flashing during the observation of the fundus in FAG and during the operation of recording the moving image, are not displayed during the reproduction. Therefore, the control described above can prevent the situation in which the desired fundus portion cannot be confirmed since the index images Pa' and Pb' overlap the fundus images F1 to F5 when the image is to be interpreted.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-111212 filed Apr. 30, 2009, which is hereby incorporated by reference herein in its entirety.

What is claimed is:

1. An ophthalmologic photographing apparatus comprising:
an imaging unit configured to capture a fundus image of a subject's eye to output an image signal;
a projection unit configured to intermittently project an index light flux onto the subject's eye in synchronization with the image signal from the imaging unit; and
an image recording unit configured to record the image signal from the imaging unit as a moving image.

2. The ophthalmologic photographing apparatus according to claim 1, wherein the projection unit is capable of changing a projection period of the index light flux.

3. The ophthalmologic photographing apparatus according to claim 2, further comprising a projection condition recording unit configured to record a projection condition of the index light flux from the projection unit in association with the image signal from the imaging unit.

4. The ophthalmologic photographing apparatus according to claim 3, further comprising a moving image reproduction unit configured to reproduce the moving image recorded by the image recording unit,
wherein the moving image reproduction unit is configured to reproduce only an image on which the index light flux is not projected based on the projection condition recorded by the projection condition recording unit.

5. The ophthalmologic photographing apparatus according to claim 4, wherein the moving image reproduction unit is configured to reproduce images including an image on which the index light flux is projected.

6. The ophthalmologic photographing apparatus according to claim 3, further comprising a moving image reproduction unit configured to reproduce the moving image recorded by the image recording unit,
wherein the moving image reproduction unit is configured to reproduce an image obtained at a timing corresponding to an image on which the index light flux is projected using an immediately previous image on which the index light flux is not projected, based on the projection condition recorded by the projection condition recording unit.

7. The ophthalmologic photographing apparatus according to claim 1, wherein the projection unit is capable of changing a projection cycle of the index light flux.

* * * * *